United States Patent
Urry

(10) Patent No.: US 12,226,596 B2
(45) Date of Patent: Feb. 18, 2025

(54) MAGNETIC FIELD DIRECTION DETECTION

(71) Applicant: Bard Access Systems, Inc., Salt Lake City, UT (US)

(72) Inventor: Robin Scott Urry, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 515 days.

(21) Appl. No.: 17/461,416

(22) Filed: Aug. 30, 2021

(65) Prior Publication Data

US 2022/0062586 A1 Mar. 3, 2022

Related U.S. Application Data

(60) Provisional application No. 63/072,697, filed on Aug. 31, 2020.

(51) Int. Cl.
*A61M 25/01* (2006.01)

(52) U.S. Cl.
CPC . *A61M 25/0127* (2013.01); *A61M 2025/0166* (2013.01); *A61M 2205/3317* (2013.01); *A61M 2205/3561* (2013.01); *A61M 2205/583* (2013.01); *A61M 2205/6054* (2013.01)

(58) Field of Classification Search
CPC ...... A61M 25/0127; A61M 2025/0166; A61M 2205/3317; A61M 2205/3561; A61M 2205/583; A61M 2205/6054
See application file for complete search history.

(56) References Cited

U.S. PATENT DOCUMENTS

| | | |
|---|---|---|
| 3,873,914 A | 3/1975 | Kesselring |
| 4,072,200 A | 2/1978 | Morris et al. |
| 4,380,735 A | 4/1983 | Bell |

(Continued)

FOREIGN PATENT DOCUMENTS

| | | |
|---|---|---|
| JP | H10230016 A | 9/1998 |
| WO | 9750000 A2 | 12/1997 |
| WO | 2017/210019 A1 | 12/2017 |

OTHER PUBLICATIONS

PCT/US2021/048263 filed Aug. 30, 2021 International Search Report and Written Opinion dated Jan. 12, 2022.

*Primary Examiner* — Baisakhi Roy
(74) *Attorney, Agent, or Firm* — Rutan & Tucker LLP

(57) ABSTRACT

A system for magnetic field direction detection when placing a catheter is disclosed, including a sensor configured to track a medical device, the sensor including a magnetic sensor printed circuit board including a plurality of magnetometers arranged in a magnetometer array. The system can include a console coupled to the sensor, including a processor and non-transitory computer-readable medium having stored a plurality of logic modules that when executed by the processor, are configured to perform operations including receiving detected magnetic field strength values detected by the plurality of magnetometers, determining a position on the sensor of each of the plurality of magnetometers, determining the magnetic field source direction based on the detected magnetic field strength values and the position on the sensor of each of the plurality of magnetometers, and displaying the magnetic field source direction on the display.

18 Claims, 5 Drawing Sheets

(56) References Cited

U.S. PATENT DOCUMENTS

| | | |
|---|---|---|
| 4,386,318 A | 5/1983 | Burbank et al. |
| 4,623,842 A | 11/1986 | Bell et al. |
| 4,913,152 A | 4/1990 | Ko et al. |
| 5,117,071 A | 5/1992 | Greanias et al. |
| 5,122,744 A | 6/1992 | Koch |
| 5,187,436 A | 2/1993 | Mallick |
| 5,437,276 A | 8/1995 | Takada |
| 5,444,372 A | 8/1995 | Wikswo, Jr. et al. |
| 6,187,032 B1 | 2/2001 | Ohyu et al. |
| 6,230,037 B1 | 5/2001 | Tsukada et al. |
| 6,424,853 B1 | 7/2002 | Tsukada et al. |
| 6,745,063 B2 | 6/2004 | Tsukada et al. |
| 6,853,185 B2 | 2/2005 | Tsukamoto et al. |
| 6,977,504 B2 | 12/2005 | Wright et al. |
| 7,026,927 B2 | 4/2006 | Wright et al. |
| 7,095,226 B2 | 8/2006 | Wan et al. |
| 7,319,321 B2 | 1/2008 | Murray et al. |
| 7,375,529 B2 | 5/2008 | Dupuis et al. |
| 7,400,984 B2 | 7/2008 | Kandori et al. |
| 7,538,715 B2 | 5/2009 | Langford et al. |
| 7,656,159 B2 | 2/2010 | Edelstein |
| 7,668,581 B2 | 2/2010 | Kandori et al. |
| 7,684,849 B2 | 3/2010 | Wright et al. |
| 7,839,140 B2 | 11/2010 | Holmstrom |
| 7,999,533 B2 | 8/2011 | LaCroix |
| 8,200,314 B2 | 6/2012 | Bladen et al. |
| 8,314,608 B2 | 11/2012 | Hall et al. |
| 8,388,541 B2 | 3/2013 | Messerly et al. |
| 8,575,929 B1 | 11/2013 | Wiegert |
| 8,781,555 B2 | 7/2014 | Burnside et al. |
| 8,849,382 B2 | 9/2014 | Cox et al. |
| 9,521,961 B2 | 12/2016 | Silverstein et al. |
| 9,526,440 B2 | 12/2016 | Burnside et al. |
| 9,549,685 B2 | 1/2017 | Cox et al. |
| 9,636,031 B2 | 5/2017 | Cox |
| 9,649,048 B2 | 5/2017 | Cox et al. |
| 9,681,823 B2 | 6/2017 | Messerly et al. |
| 9,791,536 B1 | 10/2017 | Alem et al. |
| 9,999,371 B2 | 6/2018 | Messerly et al. |
| 10,105,121 B2 | 10/2018 | Burnside et al. |
| 10,165,962 B2 | 1/2019 | Messerly et al. |
| 10,238,418 B2 | 3/2019 | Cox et al. |
| 10,393,827 B2 * | 8/2019 | Lacouture .......... G01R 33/0094 |
| 10,602,958 B2 | 3/2020 | Silverstein et al. |
| 10,806,375 B2 * | 10/2020 | Ortega .................. A61B 5/389 |
| 11,413,429 B2 * | 8/2022 | Shevgoor ................ A61L 29/14 |
| 2007/0015960 A1 | 1/2007 | Gornert et al. |
| 2007/0167723 A1 | 7/2007 | Park et al. |
| 2010/0102809 A1 | 4/2010 | May |
| 2012/0041297 A1 | 2/2012 | McGary |
| 2015/0031964 A1 * | 1/2015 | Bly ....................... A61B 5/681 |
| | | 600/300 |
| 2015/0297114 A1 | 10/2015 | Cox et al. |
| 2016/0018485 A1 | 1/2016 | Hautson et al. |
| 2016/0370441 A1 | 12/2016 | Goodson et al. |
| 2017/0079548 A1 | 3/2017 | Silverstein et al. |
| 2017/0315094 A1 | 11/2017 | Timmons et al. |
| 2017/0347913 A1 * | 12/2017 | Isaacson ............. A61B 8/0841 |
| 2017/0347914 A1 * | 12/2017 | Isaacson ............. A61B 8/0841 |
| 2017/0348509 A1 | 12/2017 | Burkholz et al. |
| 2017/0348511 A1 | 12/2017 | Burkholz et al. |
| 2018/0221610 A1 * | 8/2018 | Larson .................. H04N 7/183 |
| 2019/0239976 A1 * | 8/2019 | McClellan ............ A61B 5/062 |

* cited by examiner

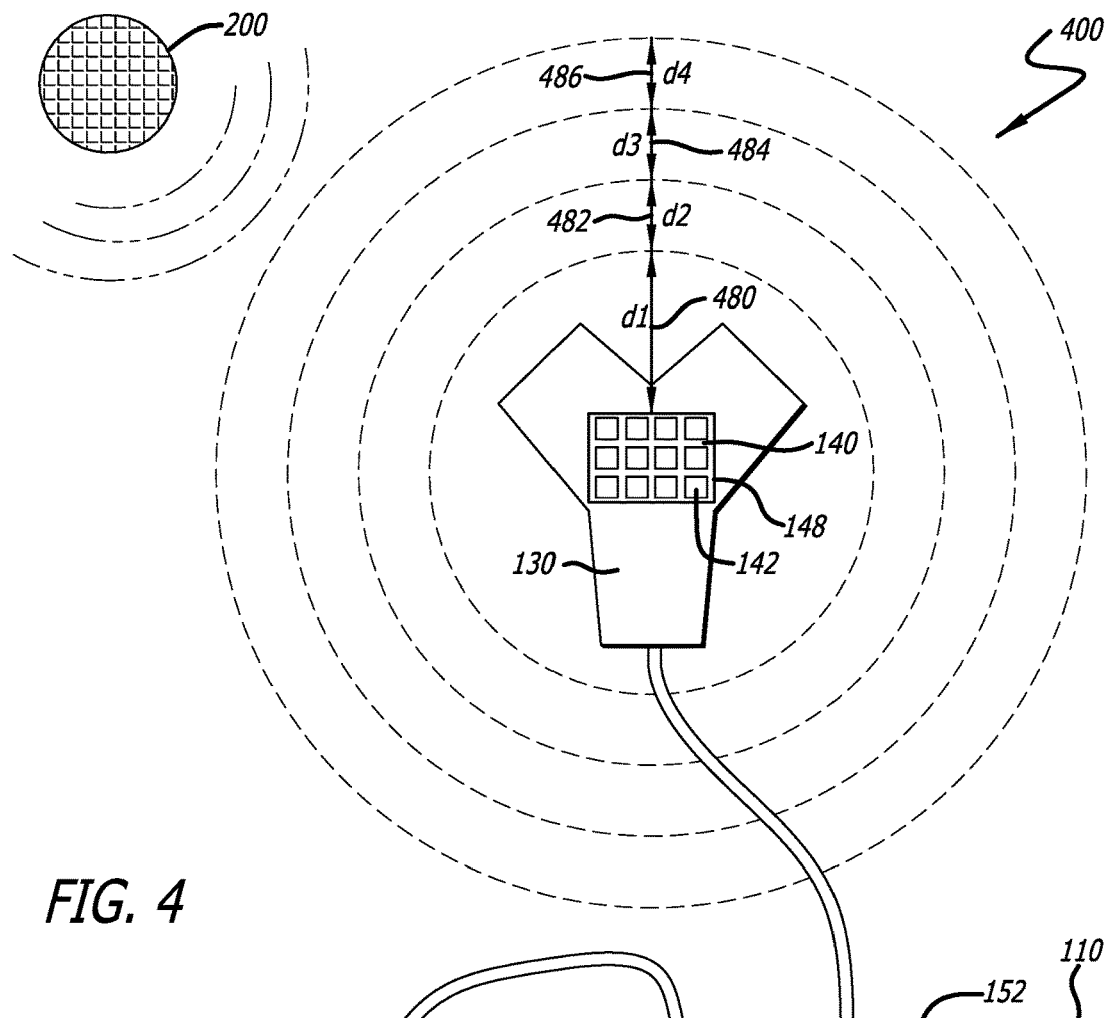
FIG. 4
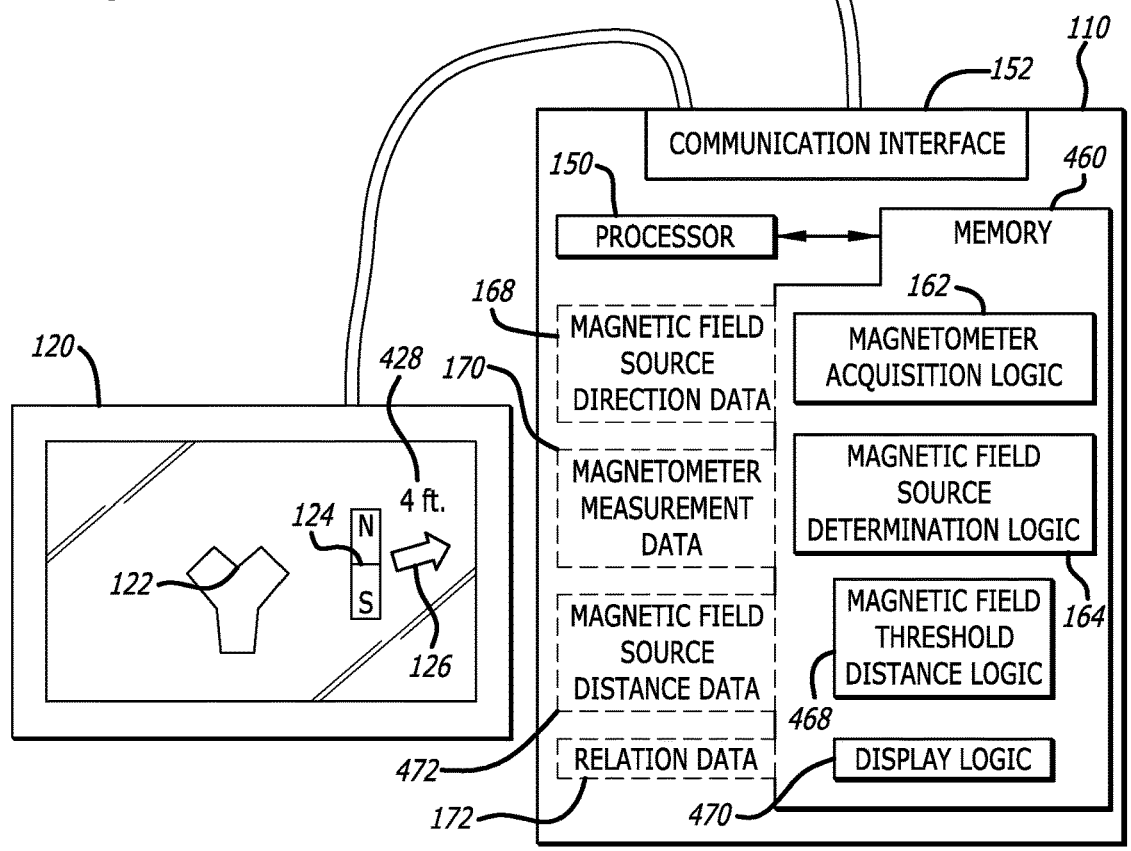

MAGNETIC FIELD DIRECTION DETECTION

PRIORITY

This application claims the benefit of priority to U.S. Provisional Application No. 63/072,697, filed Aug. 31, 2020, which is incorporated by reference in its entirety into this application.

BACKGROUND

Some medical procedures such as magnetic resonance imaging and remote catheter navigation use a magnetic field. The presence of other magnetic fields during these procedures can cause interference, which can affect correct imaging and placement of various medical devices. It would be beneficial to quickly identify if magnetic and electro-magnetic interference is present before these procedures take place as well as the direction of magnetic and electro-magnetic interference. Disclosed herein are a system, apparatus and method of use that addresses the foregoing.

SUMMARY

Disclosed herein is a system for magnetic field direction detection when placing a catheter including, in some embodiments, a sensor configured to track a medical device, the sensor including a magnetic sensor printed circuit board (PCB) including a plurality of magnetometers arranged in a magnetometer array, and a console coupled to the sensor. The console includes a processor and non-transitory computer-readable medium having stored there a plurality of logic modules that, when executed by the processor, are configured to perform operations including receiving magnetic field strength values detected by the plurality of magnetometers, determining a position on the sensor of each of the plurality of magnetometers, determining a direction of a magnetic field source relative to the sensor based on the detected magnetic field strength values and the position on the sensor of each of the plurality of magnetometers, and generating a graphic configured to illustrate the direction of the magnetic field source on a display.

In some embodiments, the system includes determining the position on the sensor of each of the plurality of magnetometers is based on a magnetometer ID of each of the plurality of magnetometers arranged in the magnetometer array.

In some embodiments, the system includes a console that correlates each magnetometer ID with the magnetic field strength value measured at each of the plurality of magnetometers within the magnetometer array.

In some embodiments, the system includes a magnetic sensor PCB provides to the console, a magnetometer ID corresponding to each of the plurality of magnetometers arranged in the magnetometer array.

In some embodiments, the system includes a console wired to the sensor.

In some embodiments, the system includes a console wirelessly coupled to the sensor.

In some embodiments, the system includes a console in communication with the display.

In some embodiments, the system includes a console including one or more thresholds corresponding to a measured strength of the magnetic field source at a known distance from the sensor.

In some embodiments, the sensor is configured to be placed on a body of a patient and perform a medical device tip location tracking process.

Also disclosed is an apparatus for magnetic field direction detection when placing a catheter including a sensor housing, a magnetic sensor printed circuit board (PCB), coupled to the sensor housing, having a plurality of magnetometers arranged in a magnetometer array, where the magnetic sensor PCB provides, to a console device, a magnetic field strength value detected by each magnetometer and a magnetometer ID of a corresponding magnetometer where the magnetic field strength values and corresponding magnetometer IDs indicate a direction of the magnetic field source relative to the apparatus based on a positioning of each magnetometer and the magnetic field strength value detected by each magnetometer.

In some embodiments, the apparatus includes a PCB including a rectangular arranged magnetometer array.

In some embodiments, the apparatus includes a PCB including an elliptical arranged magnetometer array.

Also disclosed is a method for detecting a magnetic field before placing a catheter including detecting a magnetic field by a sensor configured to track a medical device, the sensor including a magnetic sensor printed circuit board (PCB) including a plurality of magnetometers arranged in a magnetometer array, correlating the detected magnetic field strength values with a position on the sensor of each of the plurality of magnetometers as arranged in the magnetometer array, determining a direction of the magnetic field source relative to the sensor, wherein the determining is based on the correlating of the detected magnetic field strength values and the position on the sensor of each of the plurality of magnetometers, and generating a graphic configured to illustrate the direction of the magnetic field source on a display.

In some embodiments, the method includes detecting a magnetic field by a sensor includes recording an identifier of each magnetometer in the plurality of magnetometers and detected magnetic field strength value at each magnetometer in the plurality of magnetometers.

In some embodiments, the method includes generating a graphic includes generating one or more of a reference icon, a magnetic field source icon or a magnetic field source direction icon.

In some embodiments, generating a graphic includes generating a graphic that illustrates the magnetic field source is no longer detected by the sensor.

In some embodiments, generating a graphic includes generating a graphic that receives user input confirming the magnetic field source has been removed.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4 illustrates a plan view of a system for magnetic field direction detection when placing a catheter including one or more thresholds correlating to the measured strength of magnetic field source, in accordance with some embodiments.

DESCRIPTION

Figure 1:
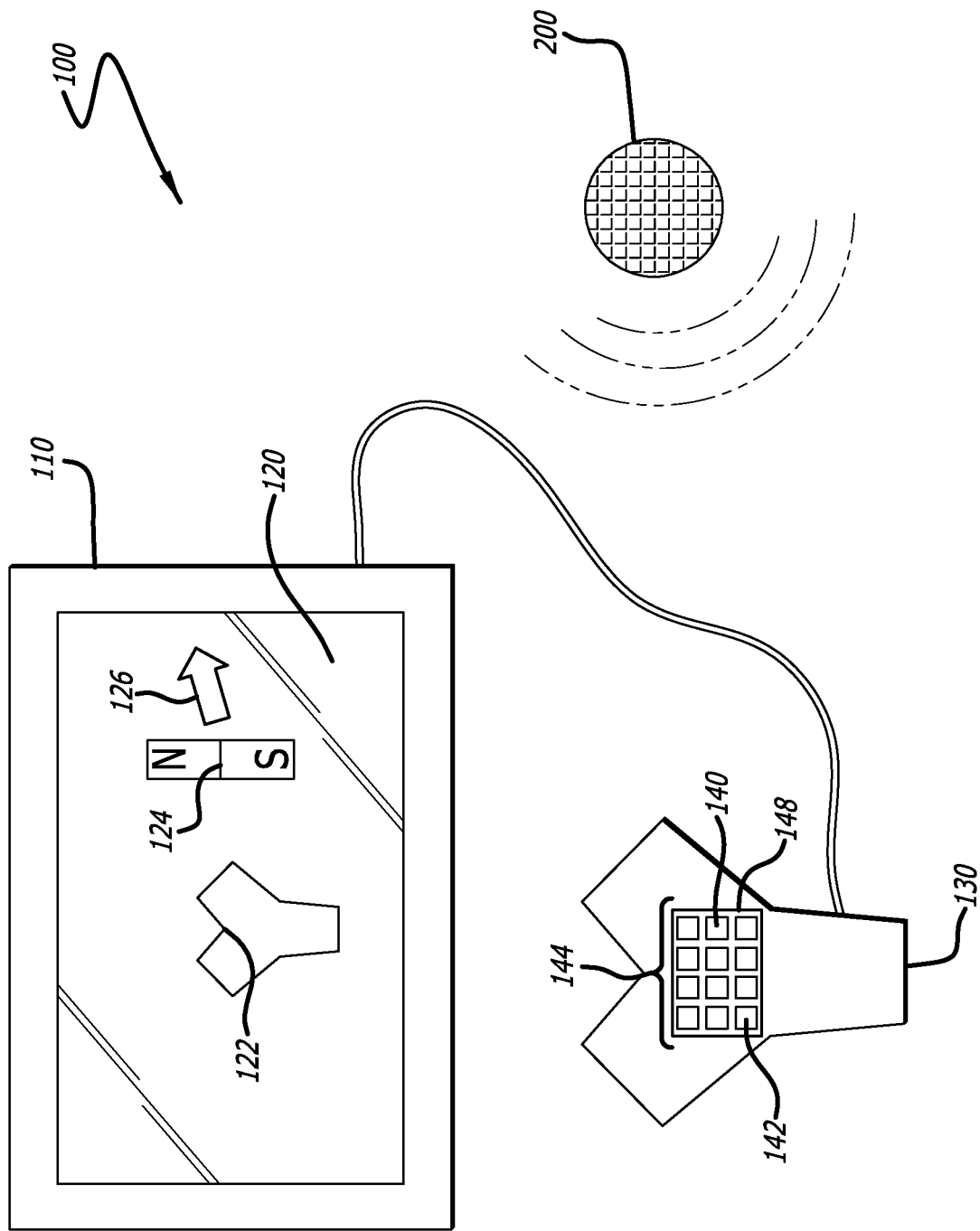
FIG. 1 illustrates a plan view of a system for magnetic field direction detection when placing a catheter including a console, a sensor including a magnetic sensor printed circuit board having a plurality of magnetometers within a magnetometer array, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

Unless defined otherwise, all technical and scientific terms used herein have the same meaning as commonly understood by those of ordinary skill in the art.

FIG. 1 illustrates a plan view of a system 100 for magnetic field direction detection when placing a catheter including a console 110 coupled to a sensor 130 including a magnetic sensor printed circuit board ("PCB") 140 with a plurality of magnetometers 142 in a magnetometer array 144, in accordance with some embodiments. In some embodiments, the system 100 includes the console 110 having a processor 150 and non-transitory computer readable medium ("memory") 160 having a plurality of logic modules that are configured to perform operations that will be described in more detail. In some embodiments, the console 110 can be coupled to a display 120 on which graphics can be generated to illustrate the direction of a magnetic field source 200 including one or more of a sensor icon 122, a magnetic field source icon 124, or a magnetic field source direction icon 126. In some embodiments, the sensor 130 may be configured to be placed on a body of a patient and perform a medical device tip location tracking process. In some embodiments, the sensor 130 includes a sensor housing 148 coupled to the magnetic sensor PCB 140 having a plurality of magnetometers 142 arranged in a magnetometer array 144 configured to detect the presence of a magnetic field source 200 through detection of a magnetic field generated thereby.

The magnetic sensor PCB 140 may be configured such that each of the plurality of magnetometers 142 in a magnetometer array 144 measures a magnetic field strength, where each measurement is communicated to the console 110. The magnetic sensor PCB 140 communicates a series of magnetic field strength measurements (e.g., values) with a magnetometer ID of the corresponding magnetometer 142 in the magnetometer array 144 to the console 110. In some embodiments, the console 110 may be configured to receive the magnetic field strength measurements from the plurality of magnetometers 142 and to determine the direction of the magnetic field source 200 based on the received magnetic field strength measurements. Once the console 110 has determined the direction of the magnetic field source 200, the console 110 may be configured to indicate the direction of the magnetic field source 200 on the display 120 through generating a graphic that may include one or more of the reference icon 122, the magnetic field source icon 124 or the direction icon 126. In some embodiments, the reference icon 122 can include an icon of a sensor, a rectangle, an X, a circle, or the like. In some embodiments, the magnetic field source icon 124 can include an icon of a bar magnet, an icon of a horseshoe magnet, an icon of a cylindrical magnet or the like. In some embodiments, the direction icon 126 can include an arrow, a line, a finger or the like. In some embodiments, the reference icon 122 may be configured to be centered on the display 120 with the magnetic field source icon 124 and the direction icon 126 being located 360° around the reference icon 122, with the direction icon 126 being displayed in the direction the console 110 has determined for the magnetic field source 200 (see FIG. 4).

Figure 2:
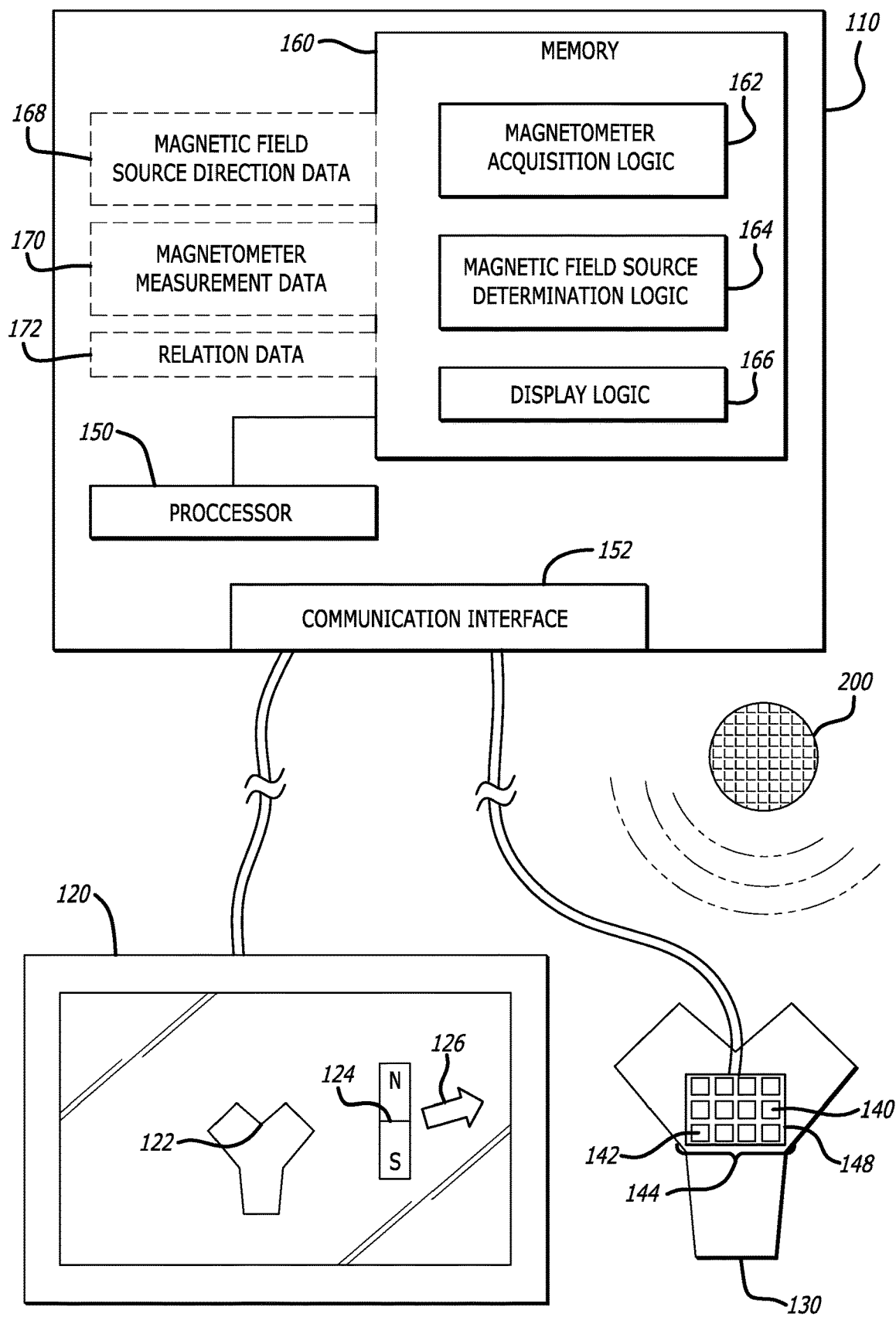
FIG. 2 illustrates a block diagram depicting various elements of a system for magnetic field direction detection when placing a catheter including a console and the sensor having a magnetic sensor PCB with a plurality of magnetometers in a magnetometer array, in accordance with some embodiments.

FIG. 2. illustrates a block diagram depicting various elements of the system for magnetic field direction detection when placing a catheter including the console 110 and the sensor 130 including the magnetic sensor PCB 140 coupled to the sensor housing 148, having a plurality of magnetometers 142 arranged in a magnetometer array 144. The console 110 is shown to include one or more processors 150, a communication interface 152, the display 120 and the memory" 160, having a plurality of logic modules including a magnetometer acquisition logic 162, a magnetic field source determination logic 164 and a display logic 166. In some embodiments, the console 110 includes the memory 160, which when executed by the processor 150 can be configured to perform operations including receiving magnetic field strength values detected by the plurality of magnetometers 142, determining a position on the sensor of each of the plurality of magnetometers 142, determining a direction of a magnetic field source 200 relative to the sensor 130 based on the detected magnetic field strength values and the position on the sensor 130 of each of the plurality of magnetometers 142, and generating a graphic configured to illustrate the direction of the magnetic field source 200 on the display 200. Further, the memory 160 may optionally include data stores such as magnetic field source direction data 168, magnetometer measurement data 170 and the relation data 172.

In some embodiments, the magnetometer acquisition logic 162 receives communications from the sensor 130 including the magnetic sensor PCB 140, wherein the communications may be a series of magnetic field strength measurement values paired with a magnetometer ID of the corresponding magnetometer 142 in the magnetometer array 144. In some embodiments, the communication may also include a location within the magnetometer array 144 along with the magnetic field strength measurement value and the magnetometer ID (i.e. a tuple). Alternatively, the magnetometer acquisition logic 162 performs a lookup for the location of a magnetometer 142 in the magnetometer array 144 based on the magnetometer ID in order to complete the {magnetic field strength, magnetometer ID, magnetometer location} tuple. In some embodiments, the magnetometer ID corresponds to the physical location of each of the plurality of magnetometers 142 in the magnetometer array 144. In some embodiments, the magnetometer acquisition logic 162 may be configured to determine the position on the sensor 130 of each of the plurality of magnetometers 142 based on the magnetometer ID of each of the plurality of magnetometers 142 arranged in the magnetometer array 144.

In some embodiments, the magnetic field source determination logic 166 determines the magnetic field source direction, relative to the sensor 130, using the magnetometer ID from each of the plurality of magnetometers 142 and the measured magnetic field strength values by each magnetometer 142. For instance, in some embodiments, the magnetic field source determination logic 166 determines a direction of the magnetic field source 200 relative to the sensor 130, using at least one threshold that will be described in more detail herein. In some embodiments, the magnetic field source determination logic 166 correlates each magnetometer ID with the magnetic field strength value measured at each of the plurality of magnetometers 142 within the magnetometer array 144. In some embodiments, the display logic 168 is configured to generate a graphic configured to illustrate the direction of the magnetic field source direction on the display 120 using one of a plurality of icons including the reference icon 122, the magnetic field source icon 124 or a magnetic field source direction icon 126.

In some embodiments, the processor 150 includes non-volatile memory such as EEPROM for instance, thus acting as a control processor. The display 120 in the present embodiment may be integrated into the console 110 and is used to display information about a magnetic field source 200 to the clinician while using the system 100. In another embodiment, the display 120 may be separate from the console 110 and may be communicatively coupled by way of a wired communication or a wireless communication including WiFi, Bluetooth, Near Field Communications (NFC), electromagnetic (EM), radio frequency (RF), combinations thereof, or the like.

In some embodiments, the sensor 130 including the magnetic sensor PCB 140 is coupled to the console 110. In some embodiments, the sensor 130 including the magnetic sensor PCB 140 can be in wired communication with the console 110. In some embodiments, the console 110 including the magnetic sensor PCB 140 can be communicatively coupled by way of wireless communication. Exemplary wireless communication modalities can include WiFi, Bluetooth, Near Field Communications (NFC), electromagnetic (EM), radio frequency (RF), combinations thereof, or the like.

Figure 3A:
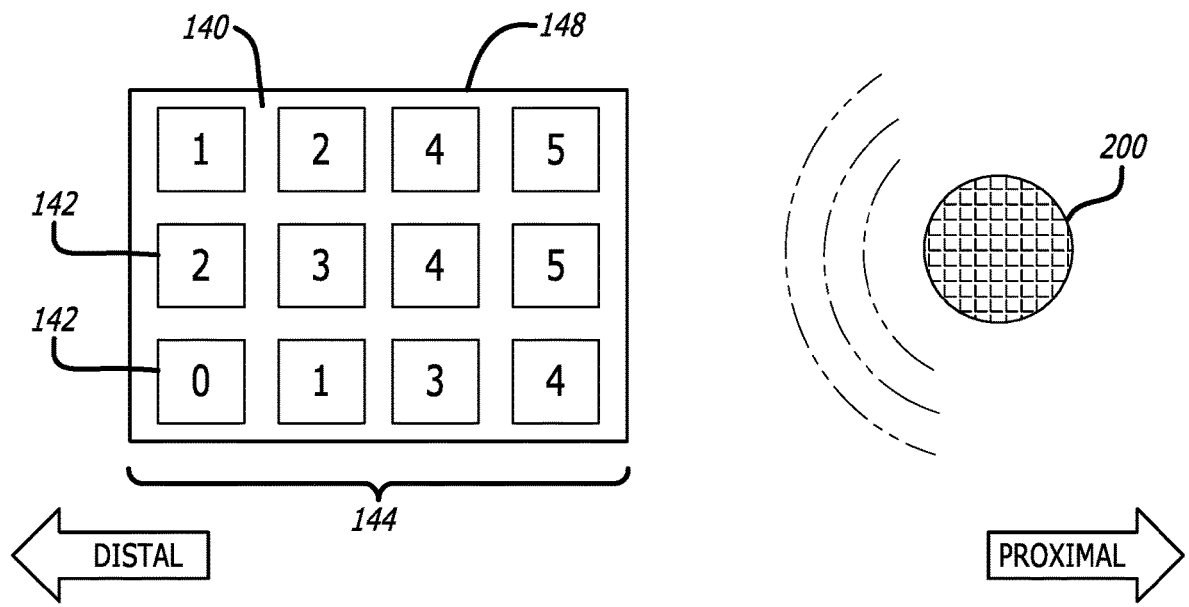
FIG. 3A illustrates a plan view of a magnetic sensor PCB with a rectangular magnetometer array measuring a magnetic field source, in accordance with some embodiments.
Figure 3B:
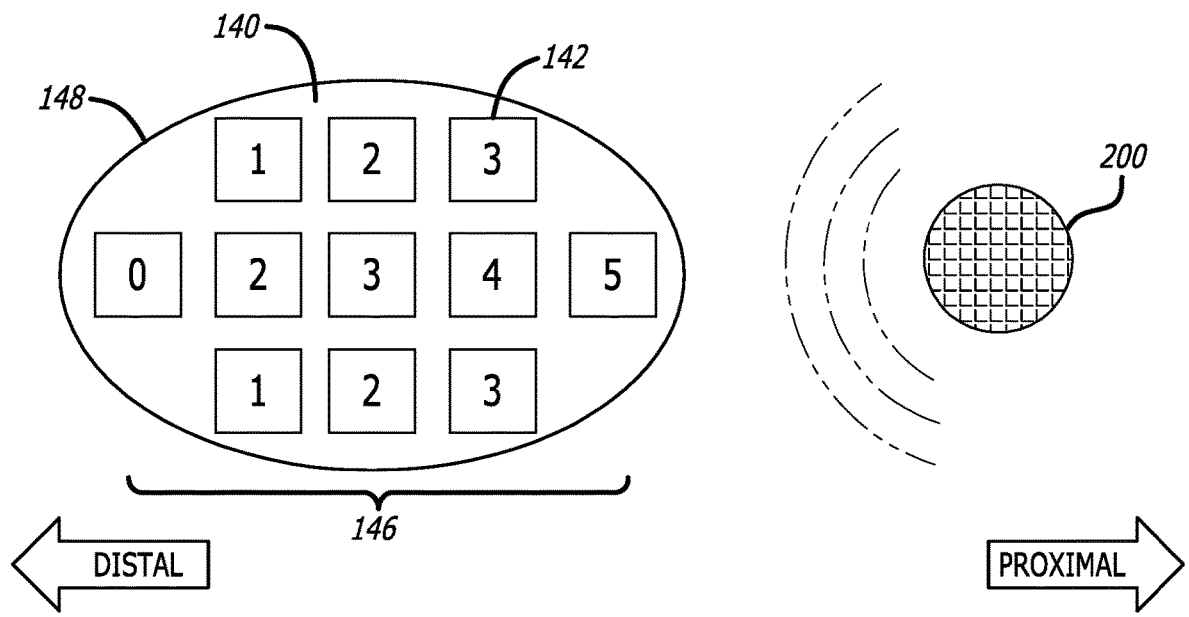
FIG. 3B illustrates a plan view of a magnetic sensor PCB with an elliptical magnetometer array measuring a magnetic field source, in accordance with some embodiments.

In some embodiments, the magnetic sensor PCB 140, coupled to the sensor housing 148, can include a plurality of magnetometers 142 arranged in various configurations in a magnetometer array 144. As illustrated in FIG. 3A, the plurality of magnetometers 142 can be arranged in a rectangular configuration on the magnetic sensor PCB 140, coupled to the sensor housing 148. If a magnetic field source 200 is present, the plurality of magnetometers 142 in the magnetometer array 144 are each configured to measure the magnetic field source strength. If a magnetic field source 200 is located on the proximal side of the magnetic sensor PCB 140, as illustrated in FIG. 3A, the plurality of magnetometers 142 located proximal the magnetic field source 200 will detect higher magnetic field strength values as compared to the plurality of magnetometers 142 located distal the magnetic field source 200, which will detect lower magnetic field strength values. In an alternative embodiment, the plurality of magnetometers 142 can be arranged in an elliptical configuration magnetometer array 146 on the magnetic sensor PCB 140 coupled to the sensor housing 148, as illustrated in FIG. 3B.

In some embodiments, a system 400 for magnetic field direction detection when placing a catheter can detect the direction of the magnetic field source 200 and distance of the magnetic field source 200. FIG. 4 illustrates a block diagram depicting various elements of the system 400 for magnetic field direction detection when placing a catheter including one or more distance thresholds correlating to the measured strength of the magnetic field source at different distances in relation to the sensor 130, in accordance with some embodiments. In this embodiment, the system 400 includes the console 110 including the processor 150 and memory 460 having stored thereon a plurality of logic modules that, when executed by the processor 150 are configured to perform operation including receiving magnetic field strength values detected by the plurality of magnetometers 142, determining the position on the sensor 130 including the magnetic sensor PCB 140 coupled to the sensor housing 148, of each of the plurality of magnetometers 142, determining the direction of a magnetic field source 200 relative to the sensor 130 based on the detected magnetic field strength values and the position on the sensor 130 of each of the plurality of magnetometers 142, determining a distance, relative to the sensor 130, based on one or more thresholds, and generating the graphic configured to illustrate the direction of the magnetic field source 200 on a display 120. In some embodiments, the console 110 is shown to include the one or more processors 150, the communication interface 152, the display 120 and the non-transitory, computer-readable medium ("memory") 460. In some embodiments, the memory 460 is configured to store logic modules including the magnetometer acquisition logic 162, the magnetic field source determination logic 166, a magnetic field threshold distance logic 468, and a display logic 470. Further, the memory 460 may optionally include data stores such as the magnetic field source direction data 170, a magnetic field source distance data 472, the magnetometer measurement data 172 and the relation data 174.

In this embodiment, the magnetometer acquisition logic 162 and the magnetic field source determination logic 166 function as described above. In this embodiment, the magnetic field threshold distance logic 468 compares a magnetic field reading from the plurality of magnetometers 142 in the magnetometer array 144 to one or more established thresholds corresponding to one or more established distances of a magnetic field source 200 from the sensor 130 including the magnetic sensor PCB 140 as described above. In this embodiment, the magnetic field threshold distance logic 468 compares magnetic field reading values to a first established threshold corresponding to a magnetic field strength within a first distance 480 ("$d_1$") away from the sensor 130 including the magnetic sensor PCB 140, to a second established threshold corresponding to the magnetic field strength within a second distance 482 ("$d_2$") away from the sensor 130 including the magnetic sensor PCB 140, to a third established threshold corresponding to the magnetic field strength within a third distance 484 ("$d_3$") away from the sensor 130 including the magnetic sensor PCB 140, and a fourth established threshold corresponding to the magnetic field strength within a fourth distance 486 ("$d_4$") away from the sensor 130 including the magnetic sensor PCB 140. Although four distances corresponding to four thresholds are illustrated, the disclosure is not intended to be so limited and other thresholds corresponding to other distances are considered.

As one example, if the magnetic field strength falls within the first established threshold, the magnetic field source is within the first distance 400 from the sensor 130 including the magnetic sensor PCB 140. If the magnetic field strength falls within the third established threshold, the magnetic field source is within the third distance 404 from the sensor including the magnetic sensor PCB 140. In this embodiment, the display logic 470 is configured to generate a graphic configured to illustrate the direction of the magnetic field source direction and the distance of the magnetic field source using a plurality of icons including the reference icon 122, the magnetic field source icon 124, the magnetic field source direction icon 126, and a magnetic field source distance icon 428 on the display 120. Further, the magnetic field source direction icon 126 may indicate the distance from the sensor 130 including the magnetic sensor PCB 140 to the detected magnetic field source 200. For example, as shown in FIG. 4, the magnetic field source direction icon 126 includes the magnetic field source distance icon 428 being the text "4 ft." The indication of the distance may refer to an approximate distance between the sensor 130 and the detected magnetic field source 200, while in other embodiments, the indication of the distance may utilize one or more thresholds (e.g., "4-6 ft." where such an indication corresponds to a particular distance threshold).

In some embodiments, the system 100 may be configured to detect the direction of a local magnetic field that may interfere with magnetic tracking devices such as devices and systems for navigation and position a central venous catheter within a patient which can be found, for example, in U.S. Pat. Nos. 8,388,541; 8,781,555; 8,849,382; 9,521,961; 9,526,440; 9,549,685; 9,636,031; 9,649,048; 9,681,823; 9,999,371; 10,105,121; 10,165,962; 10,238,418; and 10,602,958, each of which is incorporated by reference in its entirety into this Applications.

For example, the system 100 may include a console 110 having logic coupled to memory 160, a display 120, and a sensor 130 including a magnetic sensor PCB 140 having a plurality magnetometers 142 arranged in a magnetometer array 144 configured to track the tip of a medical device for proper placement including in some embodiments, a stylet, a wire, or a catheter. In some placement procedures, the sensor 130 may be configured to track the tip of the medical device by measuring a local electromagnetic field. However, a hospital bed can include a remote control (e.g., a magnetic field source 200) or other electronic devices (e.g. cell phones, tables tablets), which can interfere with the sensor 130 configured to track the tip of the medical device by producing a magnetic field and potentially leading to improper placement of the medical device. The magnetic sensor PCB 140 including the plurality of magnetometers 142 arranged in the magnetometer array 144 can be configured to measure the magnetic field strength at each of the plurality of magnetometers 142 and can be communicated to the console 110. The console 110 can be configured to receive the magnetic field strength measurement values from the plurality of magnetometers 142 and determine, using the logic coupled to memory as described above, to determine the direction of the magnetic field source 200 (e.g., the hospital bed remote control) based upon the magnetic field strength measurement values. The console 110 may then alert the user by indicating the direction of the magnetic field source 200 (e.g., the hospital bed remote control) as it relates to the sensor 130 on the display 120 by the use of one or more of the reference icon 122, the magnetic field source icon 124 or the magnetic field source direction icon 126.

Figure 5:
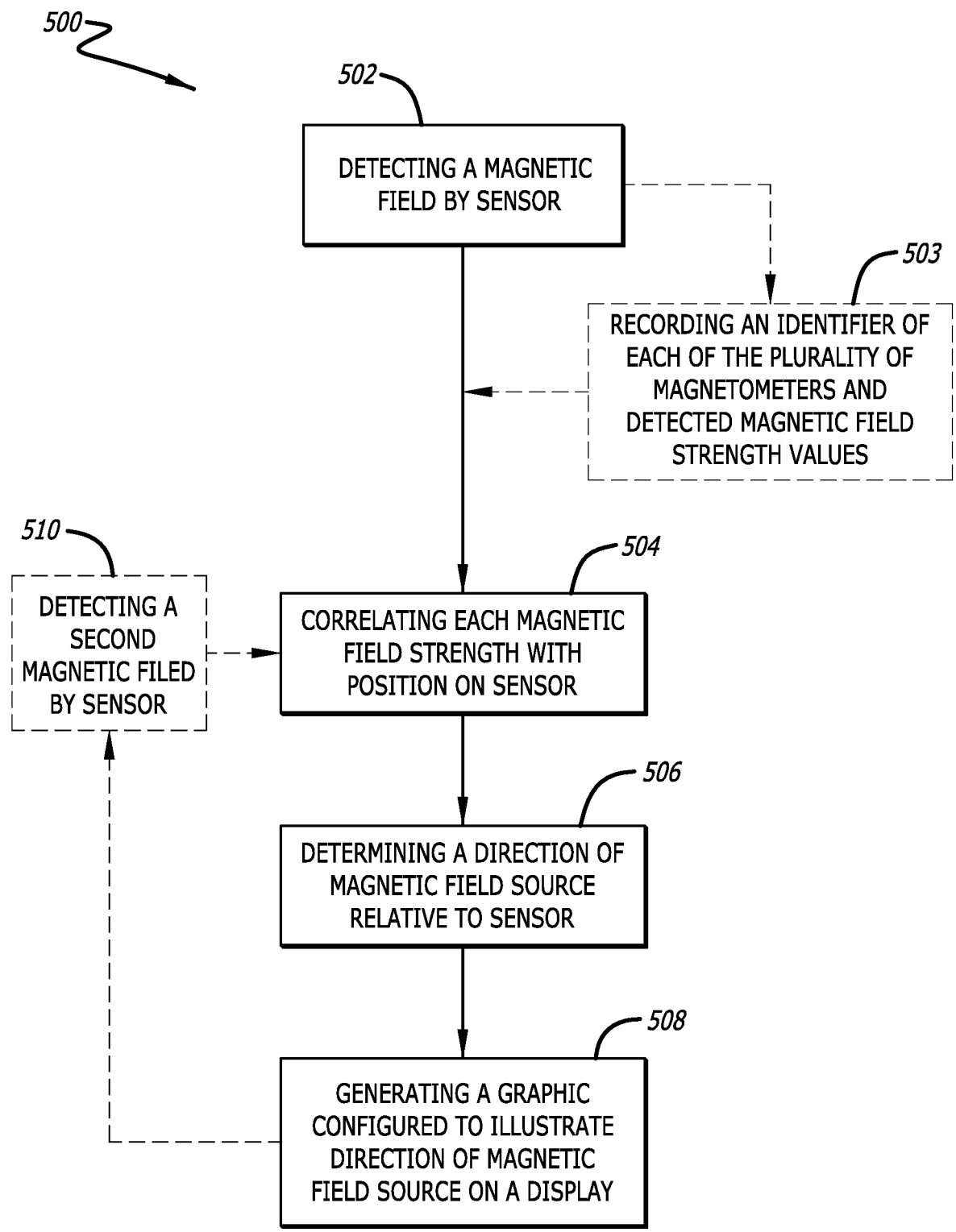
FIG. 5 illustrates an exemplary method for detecting a magnetic field before placing a catheter, in accordance with some embodiments.

FIG. 5 illustrates an exemplary method 500 of detecting a magnetic field before placing a catheter, in accordance with some embodiments. The method 500 includes detecting a magnetic field by a sensor 130 configured to be placed on a body of a patient and perform a medical device tip location tracking process, the sensor 130 including a magnetic sensor PCB 140 printed circuit board (PCB) including a plurality of magnetometers 142 arranged in a magnetometer array 144 (block 502). In some embodiments, the detecting a magnetic field by a sensor 130 includes an optional step of recording an identifier of each magnetometer in the plurality of magnetometers 142 and detected magnetic field strength value at each magnetometer in the plurality of magnetometers 142 (block 503). In some embodiments, the magnetometer array 144 may be arranged in a rectangular shape, an elliptical shape or the like. The method 500 further includes correlating the detected magnetic field strength values with a position on the sensor 130, of each of the plurality of magnetometers 142 as arranged in magnetometer array 144 (block 504). In some embodiments, the correlating includes a console 110 or the sensor 130 including the magnetic sensor PCB 140 having the plurality of magnetometers 142 arranged in a magnetometer array 144 providing a magnetometer ID that corresponds each of the plurality of magnetometers 142 in the magnetometer array 144. In some embodiments, the console 110 correlates the magnetometer ID with the magnetic field strength values measured at the one or more magnetometers 142 in the magnetometer array 144.

The method 500 further includes determining a direction of the magnetic field source 200 relative to the sensor 130, wherein the determining is based on the correlating of the detected magnetic field strength values at each of the plurality of magnetometers 142 and the position on the sensor 130 of each of the plurality of magnetometers 142 (block 506).

The method 500 further includes generating a graphic configured to illustrate the direction of the magnetic field source 200 on a display 120 (block 508). In some embodiments, the generating a graphic includes generating one or more of a reference icon 122, a magnetic field source icon 124 or a magnetic field source direction icon 126. In some embodiments, generating a graphic includes generating a graphic that the magnetic field source 200 is no longer detected by the sensor. In some embodiments, the generating a graphic includes generating a graphic that illustrates the magnetic field source 200 is no longer detected by the sensor 130 including the magnetic sensor PCB 140. In some embodiments, the generating a graphic includes generating a graphic that receives user input confirming the magnetic field source 200 has been removed. In some embodiments, the generating a graphic includes generating one or more of the reference icon 122, the magnetic field source icon 124, a magnetic field source distance icon 428 or the magnetic field source direction icon 126. In some embodiments, the optional step of detecting a second magnetic field (block 512) can occur only after generating a graphic configured to illustrate the direction of the magnetic field source 200 on the display 200 (block 508).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A system for magnetic field direction detection when placing a medical device comprising:
 a sensor configured to track the medical device, the sensor including a magnetic sensor printed circuit board (PCB) including a plurality of magnetometers arranged in a magnetometer array; and
 a console coupled to the sensor, the console including a processor and non-transitory computer-readable medium having stored thereon a plurality of logic modules that, when executed by the processor, are configured to perform operations including:
 receiving magnetic field strength values detected by the plurality of magnetometers;
 determining a position of each of the plurality of magnetometers on the sensor based on a magnetometer ID of each of the plurality of magnetometers arranged in the magnetometer array;
 determining a direction of a magnetic field source relative to the sensor based on the magnetic field strength values detected by the plurality of magnetometers and the position on the sensor of each of the plurality of magnetometers;
 generating a graphic configured to illustrate the direction of the magnetic field source on a display; and
 correlating each magnetometer ID with the magnetic field strength values measured at each of the plurality of magnetometers within the magnetometer array.

2. The system according to claim 1, wherein the magnetic sensor PCB provides to the console, the magnetometer ID corresponding to each of the plurality of magnetometers arranged in the magnetometer array.

3. The system according to claim 1, wherein the console is wired to the sensor.

4. The system according to claim 1, wherein the console is wirelessly coupled to the sensor.

5. The system according to claim 1, wherein the console is in communication with the display.

6. The system according to claim 1, wherein the console includes one or more thresholds corresponding to a measured strength of the magnetic field source, the one or more thresholds corresponding to one or more established distances of the magnetic field source from the sensor.

7. The system according to claim 1, wherein the sensor is configured to be placed on a body of a patient.

8. The system according to claim 1, wherein the magnetic field source includes an electronic device other than the medical device, the electronic device including at least one of a remote control, a cell phone, or a tablet.

9. An apparatus for magnetic field direction detection when placing a medical device comprising:
 a sensor housing; and
 a magnetic sensor printed circuit board (PCB) coupled to the sensor housing, the magnetic sensor PCB having a plurality of magnetometers arranged in a magnetometer array, wherein the magnetic sensor PCB provides, to a console device, a magnetic field strength value detected by each of the plurality of magnetometers and a magnetometer ID of each of the plurality of magnetometers correlated with corresponding detected magnetic field strength values;
 wherein the magnetic field strength value and the magnetometer ID correlated therewith indicate a direction of a magnetic field source relative to the apparatus based on a positioning of each magnetometer and the magnetic field strength value detected by each magnetometer.

10. The apparatus according to claim 9, wherein the PCB includes a rectangular arranged magnetometer array.

11. The apparatus according to claim 9, wherein the PCB includes an elliptical arranged magnetometer array.

12. The apparatus according to claim 9, wherein the magnetic field source includes an electronic device other than the medical device, the electronic device including at least one of a remote control, a cell phone, or a tablet.

13. A method for detecting a magnetic field before placing a medical device comprising:
 detecting the magnetic field by a sensor configured to track the medical device, the sensor including a magnetic sensor printed circuit board (PCB) including a plurality of magnetometers arranged in a magnetometer array;

correlating detected magnetic field strength values with a position on the sensor of each of the plurality of magnetometers as arranged in the magnetometer array;

correlating a magnetometer ID of each of the plurality of magnetometers with the detected magnetic field strength values measured at the each of the plurality of magnetometers;

determining a direction of a magnetic field source relative to the sensor, wherein the determining is based on the correlating of the detected magnetic field strength values and the position on the sensor of each of the plurality of magnetometers; and generating a graphic configured to illustrate the direction of the magnetic field source on a display.

14. The method according to claim 13, wherein detecting the magnetic field by the sensor includes recording an identifier of each magnetometer in the plurality of magnetometers and the detected magnetic field strength values at each magnetometer in the plurality of magnetometers.

15. The method according to claim 13, wherein generating the graphic includes generating one or more of a reference icon, a magnetic field source icon or a magnetic field source direction icon.

16. The method according to claim 13, wherein generating the graphic includes generating a graphic that illustrates the magnetic field source is no longer detected by the sensor.

17. The method according to claim 13, wherein generating the graphic includes generating a graphic that receives user input confirming the magnetic field source has been removed.

18. The method according to claim 13, wherein the magnetic field source includes an electronic device other than the medical device, the electronic device including at least one of a remote control, a cell phone, or a tablet.

\* \* \* \* \*